United States Patent [19]

Ott et al.

[11] Patent Number: 4,808,615

[45] Date of Patent: Feb. 28, 1989

[54] FLEA AND TICK INFESTATION CONTROL COMPOSITION CONTAINING CHLORPYRIFOS AND VINYL ACETATE/CROTONIC ACID/VINYL NEODECANOATE COPOLYMER

[75] Inventors: Bruce S. Ott, Belle Mead; Joseph Haus, East Windsor; Frederick F. Kohlhepp, Princeton Junction, all of N.J.

[73] Assignee: Carter-Wallace, Inc., New York, N.Y.

[21] Appl. No.: 725,219

[22] Filed: Apr. 19, 1985

[51] Int. Cl.[4] .............................................. A01N 57/00
[52] U.S. Cl. .................................... 514/89; 424/409; 424/411; 424/70
[58] Field of Search ................ 424/409, 411, 78, 409, 424/411, 89; 525/122; 514/345, 86, 122, 481, 531, 521, 478, 479

[56] References Cited

U.S. PATENT DOCUMENTS

| | | |
|---|---|---|
| 4,117,853 | 10/1978 | Reese et al. .................. 424/DIG. 1 |
| 4,150,109 | 4/1979 | Dick et al. ........................... 424/411 |
| 4,172,904 | 10/1979 | Young et al. ........................... 427/4 |
| 4,282,209 | 8/1981 | Tocker .................................. 424/78 |

*Primary Examiner*—Joseph L. Schofer
*Assistant Examiner*—Peter F. Kulkosky
*Attorney, Agent, or Firm*—Kevin B. Clarke

[57] ABSTRACT

A method and composition for the elimination of fleas and ticks as well as the prevention and/or control of flea and tick infestation of animals, particularly household pets, which comprises applying a substantive, controlled release, coating of a solution of a polymeric material and an insecticide to the shafts of hair of the animal's coat.

2 Claims, No Drawings

FLEA AND TICK INFESTATION CONTROL COMPOSITION CONTAINING CHLORPYRIFOS AND VINYL ACETATE/CROTONIC ACID/VINYL NEODECANOATE COPOLYMER

BACKGROUND OF THE INVENTION

This invention relates to novel methods and compositions for preventing, eliminating and/or controlling flea and tick infestation in animals, particularly household pets.

Flea and tick infestation of household pets is a perennial and often frustrating problem to pet owners.

A wide variety of products are commercially available for the treatment of fleas including spray, dips, powders, shampoos and the like which are effective in the elimination of fleas and ticks from household pets.

However, pets are readily reinfested by fleas and ticks after treatment with the above-noted products simply by returning to a flea infested environment or contact with flea infested animals.

It has been proposed to provide long term protection against flea and tick infestation by attaching to the animal insecticide, holders adapted to hold and apply liquid insecticides to the animals coat, i.e. U.S. Pat. Nos. 2,306,076 and 3,687,114. It has also been proposed to impregnate porous metal pendants or the like with insecticides which will vaporize when attached to the animal's collar and kill fleas in the surrounding area, i.e. U.S. Pat. No. 2,661,238.

It is now well established practice in the pet care industry to obtain controlled or sustained release of an insecticide system by incorporation of the insecticide into a polymeric system. A pesticide dispersed in a polymeric system is desirably released by diffusion or by plasticization and/or swelling of the polymer membrane.

In more recent times, collars have been provided for placement around the animal's neck, which are designed to provide continuous protection over a period of time. The collars are natural or synthetic materials impregnated with insecticides in powder or liquid form, which insecticides continually migrate to the collar surface and spread over the surface of the animal's skin, during the effective life of the collar, and kill fleas and ticks upon contact in the neck area of the animal, when the pests migrate towards the animal's head or the pesticide may vaporize and provide an insecticidal fog in the environment adjacent to the animal's hair shafts and skin. Representative of such collars are those disclosed in U.S. Pat. No. 3,852,416.

It has also been proposed to provide adherent, controlled release pesticide compositions which may be sprayed on an animal's coat and which provide a sustained killing effect over the useful life of the compositions, i.e. U.S. Pat. No. 4,172,904. However, such compositions do not leave the animal's coat in a soft natural condition.

SUMMARY OF THE INVENTION

In order to provide adequate control of flea infestation over substantially all of an animal's body, the insecticide compositions must meet the following criteria:

1. The composition must be adherent to the hair shafts and skin of the animal;
2. The composition must be substantive when applied to the hair shafts to the extent that it will not flake and is not easily removed by wind, rain or casual brushing or petting of the animal;
3. The composition must be readily removable from the hair shafts of the animal by washing with mildly alkaline shampoo;
4. The composition when applied to the hair shafts of the animal's hide must substantially coat the individual hair shafts and when dried, must leave the coat in an unmatted, non-tacky condition;
5. The composition must not discolor the coat of the animal;
6. The composition must effectively kill fleas and ticks over an extended period of time when applied to the shafts of hair of the animal's coat.
7. The composition must permit the hair shafts and skin of the animal to breathe, i.e., must be adequately permeable to oxygen, carbon dioxide and water vapor; and,
8. The composition must be non-toxic to the animal and human beings.

We have now found that compositions of the present invention composed basically of a solvent, a polymeric material, an insecticide and optionally plasticizers, antioxidants and ultra violet light absorbers effectively meet all of the above-noted criteria.

Accordingly, it is an object of the present invention to provide non-toxic pesticide compositions which readily adhere to the shafts of hair of an animal's coat, which may be removed from the shafts of hair of the animal's coat by washing with mildly alkaline shampoo and which continuously release, during the effective life of the composition, amounts of an insecticide adequate to exert insecticidal activity on the environment immediately surrounding the coated hair shafts.

It is a further object to provide methods of coating the shafts of hair of an animal's coat whereby insecticidal activity is provided on the environment immediately surrounding the coated hair shafts.

The insecticides which may be used in the practice include any of the compounds well-known in the art for use as insecticides so long as they are compatible with the polymer-solvent system. Some common insecticides which may be used include the following:

Chlorpyrifos, carbaryl, synthetic pyrethroids, pyrethrins, malathion, baygon, diazinon and the like.

The insecticide is present in the compositions of the present invention in amounts sufficient to exert insecticidal activity on the skin and the environment immediately surrounding the coated animal hair shaft for an extended period of time.

DETAILED DESCRIPTION OF THE INVENTION

Obviously, the amount of insecticide present will depend on many elements, i.e., the particular insecticide used, the thickness of the polymer coating when applied to the hair shaft, the duration of insecticidal activity desired, the physical state of the insecticide, etc., the optimal amount of insecticide present in the composition, based on the foregoing considerations can be readily determined by one skilled in the art.

In the preferred embodiment, the insecticide is present in amounts ranging from about 0.025% by weight to about 0.5% of the total composition, preferably about 0.25% by weight.

The solvent-carrier material used in the present invention can be any solvent for the polymeric material which is compatible with the insecticide. Desirably, the solvent is a low molecular weight essentially anhydrous alcohol such as anhydrous enthanol, propanol, isopropanol, etc., in addition to acetone and methylene chloride and combinations thereof with each other and small amounts of water. Preferably ethanol in amounts ranging from about 95.0% by weight to about 98.5% by weight of the total composition is the solvent.

The polymeric materials useful in the present invention are vinyl acetate-unsaturated acid copolymers, optionally containing other monomers, i.e. the 90/10 vinyl acetate/crotonic acid polymers and the vinyl ether-alkyl acid maeate copolymers, i.e. the 50/50 methyl vinyl ether-ethyl acid maleate copolymer. Preferably the polymeric material is a carboxylated vinyl acetate terpolymer available in the form of fine, translucent beads. Specifically, the terpolymer is a vinyl acetate/crotonic acid/vinyl neodecanoate terpolymer containing 10% crotonic acid and 90% of a mixture of vinyl acetate and vinyl neodecanonate available from National Starch and Chemical Corporation under the Trademark RESYN 28-2930. The polymeric material is present in the compositions of the present invention in amounts ranging from about 0.50% by weight to about 3.00% by weight of the total composition, preferably 1.00% by weight to about 2.50% by weight of the total composition.

In addition to the foregoing, the compositions of the present invention may include additional ingredients such as fragrances, antioxidants, ultraviolet light stabilizers, plasticizers, synergists and the like, it being found particularly desirable to add plasticizers such as petroleum base oil, dibutyl phthalate, dioctyl phthalate, dibutoxy ethyl phthalate, diamyl phthalate, castor oil, soybean oil and lanolin oil as well as ultraviolet light absorbers such as 2-hydroxy-4-octyloxybenzophenone and antioxidants such as 3-(3'5'-di-t-butyl-4'-hydroxyphenyl) proprionate and insecticide synergists such as piperonyl butoxide which may be present in amounts ranging from zero to about 1.5% preferably 0.25% to about 1.00% by weight of the composition.

The preparation of the compositions of the present invention is carried out according to the following procedure:

1. Charge mixing vessel with solvent (60°–70° F.)
2. Begin agitation and slowly add resin material until all solids are in solution.
3. Add insecticide and optionally, the plasticizer and other ingredients such as antioxidants and ultraviolet light stabilizers.
4. Filter and pack into bottles preferably equipped with pump spray applicators.

EXAMPLES

To test the effective killing power of the compositions of the present invention against live fleas and ticks, the following formulations were prepared in the foregoing manner:

EXAMPLE NOS. 1-4

| Ingredient | 1 | 2 | 3 | 4 |
|---|---|---|---|---|
| RESYN 28-2930 | 2.50% | 2.50% | 1.00% | 1.00% |
| Chlorpyrifos | 0.25% | 0.25% | 0.50% | 0.50% |
| Ethyl alcohol (anhydrous) | 96.75% | 96.75% | 98.25% | 98.15% |
| Epoxidized Soybean Oil | — | — | — | 0.1% |
| Cetearyl Octanoate | 0.25% | — | — | — |
| Lanolin Oil | 0.25% | — | — | — |
| Fragrance | 0.25% | 0.25% | 0.25% | 0.25% |

The formulations were put up in 8 oz. high density polyethylene bottles fitted with sprayers, orifice size 0.025, delivery per stroke 0.85CC. Samples were weighed before and after application and the weight of material delivered recorded.

A 9 Kg. long-haired, white dog was used to test the effectiveness of the compositions. The back of the dog was marked off into four approximately equal surface areas labeled A, B, C and D respectively. Example 1 was applied to Site A, Example 2 was applied to Site B, Example 3 was applied to Site C and Example 4 was applied to Site D. Each site was sprayed until thoroughly wetted to the skin (approximately 9–14 grams of material). When the coat was completely dry, the dog was combed out and approximately 0.5 grams of hair was clipped from each site and placed into a 4 dram screw cap vial containing live fleas. Additional samples were taken from each site on day 30, 57 and 89 and similarly exposed to live fleas.

The observed flea kills for the examples are given in Table No. 1:

TABLE NO. 1

| Example No. | Initial | 30 Days | 57 Days | 84 Days |
|---|---|---|---|---|
| 1 | 100% | 100% | 100% | 75% |
|  | 30 min. | 6–18 hrs. | 24 hrs. | 48 hrs. |
| 2 | 100% | 100% | 100% | 95% |
|  | 30 min. | 6 hrs. | 18 hrs. | 48 hrs. |
| 3 | 100% | 100% | 100% | 95% |
|  | 30 min. | 18 hrs. | 24 hrs. | 24 hrs. |
| 4 | 100% | 100% | 100% | 95% |
|  | 30 min. | 24 hrs. | 24 hrs. | 24 hrs. |

Numerous modifications and variations of the present invention are possible in light of the above teachings and therefore within the scope of the appended claims, the invention may be practiced otherwise than as particularly described.

What is claimed is:

1. A liquid composition for direct application to the skin and hair of canine animals for the prevention and control of flea and tick infestation consisting of a solution of about 1.00% by weight of a terpolymer of vinyl acetate/crotonic acid/vinyl neodecanoate containing about 10% crotonic acid and 90% of a mixture of vinyl acetate and vinyl neodecanoate, about 98.5% by weight ethanol, about 0.25% by weight chlorpyrifos and about 0.25% by weight of a fragrance.

2. A method for the prolonged prevention and control of flea and tick infestation on canine animals comprising wetting the skin and hair shafts of such animals with a solution consisting of about 1.00% by weight of a terpolymer of vinyl acetate/crotonic acid/vinyl neodecanoate containing about 10% crotonic acid and 90% of a mixture of vinyl acetate and vinyl neodecanoate, about 98.5% by weight ethanol, about 0.25% by weight chlorpyrifos and about 0.25% by weight of a fragrance.

* * * * *